(12) United States Patent
Metzger et al.

(10) Patent No.: US 7,425,222 B2
(45) Date of Patent: Sep. 16, 2008

(54) PROCESS FOR IMPROVING THE SUN PROTECTION FACTOR OF CELLULOSIC FIBRE MATERIAL

(75) Inventors: Georges Metzger, Moernach (FR); Jean-Jacques Donzé, Blodelsheim (FR); Hans Kramer, Frick (CH); Serge Hauger, Ranspach-le-Bas (FR); Volker Papendick, Lörrach (DE); Michael Milde, Grenzach-Wyhlen (DE); Ted Deisenroth, Schwörstadt (DE); Rainer Hans Traber, Reinach (CH); Ullrich Menge, Grenzach-Wyhlen (DE); Hauke Rohwer, Lörrach (DE)

(73) Assignee: Ciba Specialty Chemicals Corp., Tarrytown, NY (US)

( * ) Notice: Subject to any disclaimer, the term of this patent is extended or adjusted under 35 U.S.C. 154(b) by 504 days.

(21) Appl. No.: 10/504,945

(22) PCT Filed: Feb. 11, 2002

(86) PCT No.: PCT/EP03/01326

§ 371 (c)(1), (2), (4) Date: Aug. 16, 2004

(87) PCT Pub. No.: WO03/069047

PCT Pub. Date: Aug. 21, 2003

(65) Prior Publication Data
US 2005/0106114 A1 May 19, 2005

(30) Foreign Application Priority Data
Feb. 18, 2002 (EP) .................................. 02405118

(51) Int. Cl.
*D06L 3/12* (2006.01)

(52) U.S. Cl. .................... 8/648; 8/107; 8/116.1; 8/190; 252/8.61; 252/8.86; 252/8.91

(58) Field of Classification Search .................. 8/115.6, 8/190, 648, 107, 116.1; 252/8.61, 8.86, 8.91
See application file for complete search history.

(56) References Cited

U.S. PATENT DOCUMENTS

| | | | |
|---|---|---|---|
| 4,587,195 A * | 5/1986 | Ishikawa et al. | 430/139 |
| 5,700,295 A * | 12/1997 | Fuso et al. | 8/189 |
| 5,744,599 A * | 4/1998 | Reinehr et al. | 544/193.1 |
| 5,810,889 A * | 9/1998 | Kaufmann et al. | 8/442 |
| 5,888,643 A * | 3/1999 | Aylward et al. | 428/315.9 |
| 5,938,793 A * | 8/1999 | Reinert et al. | 8/442 |
| 6,143,888 A | 11/2000 | Rohringer et al. | 544/193.2 |
| 6,783,698 B1 | 8/2004 | Reinehr et al. | 8/648 |
| 2003/0192137 A1 | 10/2003 | Cuesta et al. | 8/518 |

FOREIGN PATENT DOCUMENTS

| | | | |
|---|---|---|---|
| EP | 0728749 | * | 8/1996 |
| EP | 0922699 | | 6/1999 |
| WO | 00/77290 | * | 12/2000 |
| WO | 02/08511 | * | 1/2002 |

* cited by examiner

Primary Examiner—Lorna M. Douyon
Assistant Examiner—Amina Khan
(74) Attorney, Agent, or Firm—Tyler A. Stevenson

(57) ABSTRACT

A process for improving the sun protection factor (SPF) of cellulosic fibre materials and blends thereof, which comprises contacting said materials with at least one compound of the formula (1)

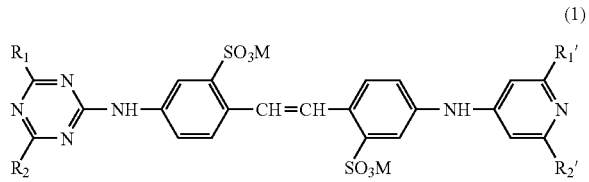

in which M is hydrogen, an alkali metal atom, ammonium or a cation formed from an amine; $R_1$ and $R_1'$ independently of each other are hydrogen, hydroxy, optionally substituted alkyl, 4-morpholinyl, —NH—$R_3$, —N($R_3$)$_2$ or —O—$R_3$, wherein $R_3$ is optionally substituted alkyl or optionally substituted aryl, $R_2$ is a group of formula (2)

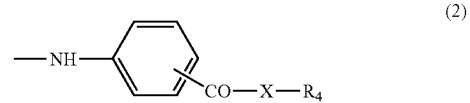

wherein X is —O— or —NH— and $R_4$ is $C_1$-$C_4$-alkyl which carries at least one hydrophilic substituent and $R_2'$ has the meaning of $R_1$ or $R_2$.

9 Claims, No Drawings

PROCESS FOR IMPROVING THE SUN PROTECTION FACTOR OF CELLULOSIC FIBRE MATERIAL

The present invention relates to a process for improving the sun protection factor (SPF) of cellulosic fibre materials and blends thereof, which comprises treating the cellulosic fibre materials with at least fluorescent whitening agent (FWA) and preferably additionally at least one reactive UV absorber. The invention moreover relates to new fluorescent whitening agents useful for that process.

The skin-damaging effect of UV radiation is well known. Protection from strong sunlight is usually sought by applying a sun cream, a composition that contains a UV absorber, directly to the skin. In particularly sunny regions, for example in Australia or America, however, the rate of skin damage due to UV radiation has recently been increasing dramatically. Accordingly, more attention is paid in these countries to protecting the skin from solar irradiation.

It has therefore been proposed that the skin should be protected not just directly, but also to reduce the UV transmissibility of the clothing and also of other sun protection articles, such as awnings or parasols. Especially cellulosic fibre materials are at least partially transparent to UV radiation, so that the mere wearing of clothing does not offer adequate protection to the skin from damage due to UV radiation. A remedy is possible here by incorporating UV absorbers and/or FWA's into the fibre material.

However, hitherto the results achieved in respect of the protection from UV radiation in the area of cellulosic fibre materials, in particular textile materials have not been completely satisfactory and there therefore continues to be a need for improving the sun protection factor of these materials. Despite the fact that this is a general problem, one specific aspect has been found especially problematic. In the case of cellulosic fibre materials treated with fluorescent whitening agents (FWA's), incorporation of UV absorbers has been found to result in loss of the whitening effect, thus leading to an undesirable yellowing of the fibres.

It has now been found that, surprisingly, a particular class of fluorescent whitening agents, especially if applied together with specific UV absorbers, not only provides excellent sun protection factors for cellulosic fibre materials in general, but also results in little or no observable reduction of the degrees of whiteness of the so-treated materials.

Correspondingly, the present invention provides a process for improving the sun protection factor (SPF) of cellulosic fibre materials and blends thereof, which comprises contacting said materials with at least one compound of formula

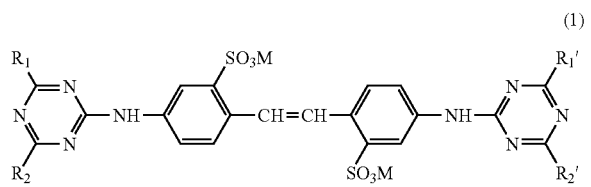

(1)

in which M is hydrogen, an alkali metal atom, ammonium or a cation formed from an amine;

$R_1$ and $R_1'$ independently of each other are hydrogen, hydroxy, optionally substituted alkyl, 4-morpholinyl, —NH—$R_3$, —N($R_3$)$_2$ or —O—$R_3$, wherein $R_3$ is optionally substituted alkyl or optionally substituted aryl, $R_2$ is a group of formula

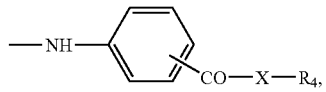

(2)

wherein X is —O— or —NH— and $R_4$ is $C_1$-$C_4$-alkyl which carries at least one hydrophilic substituent and $R_2'$ has the meaning of $R_1$ or $R_2$.

$R_2$ and $R_2'$ can have different meanings. Preferably, however, they are identical.

According to the invention, alkyl radicals are to be understood as being generally open-chain or branched alkyl radicals containing from 1 to 6 carbon atoms, for example methyl, ethyl, n- or iso-propyl, n-, sec- or tert-butyl or n-hexyl, n-octyl. Cycloalkyl is preferably cyclopentyl or cyclohexyl.

$R_3$ as aryl is preferably independently of each other phenyl or naphthyl which are unsubstituted or substituted e.g. by $C_1$-$C_6$-alkyl, $C_1$-$C_6$-alkoxy or a hydrophilic substituent.

In preferably used compounds of formula (1) $R_1$ and $R_1'$ are identical and especially preferred is the use of a compound of formula (1), wherein $R_1$ and $R_1'$ are each are hydrogen, hydroxy, optionally substituted alkyl, —NH—$R_3$, —N($R_3$)$_2$ or —O—$R_3$, wherein $R_3$ is optionally substituted alkyl or optionally substituted aryl.

Especially preferred meanings of $R_1$ and $R_1'$ are hydrogen, hydroxy, unsubstituted $C_1$-$C_4$-alkyl or $C_1$-$C_4$-hydroxyalkyl, 4-morpholinyl, —NH—$R_3$, —N($R_3$)$_2$ or —O—$R_3$, wherein $R_3$ is unsubstituted $C_1$-$C_4$-alkyl or $C_1$-$C_4$-hydroxyalkyl or unsubstituted phenyl or phenyl substituted by sulfo, $C_1$-$C_4$-alkylsulfonyl or $C_1$-$C_4$-hydroxyalkylsulfonyl.

The hydrophilic substituent in the radical $R_4$ is preferably —OM, —COOM or SO$_3$M in which M is hydrogen, an alkali metal atom, ammonium or a cation formed from an amine.

The quantities of compound (1) to be applied to the cellulosic material according to the process of the invention may vary over a wide range. However, when used in amounts of between 0.001 and 2% by weight, based on the weight of the fibre material, useful effects may be obtained. Preferably, however, the amount of the compound of formula (1) used is from 0.005 to 1% and especially from 0.01 to 0.5% by weight, based on the weight of the fibre material.

Cellulosic fibre materials are to be understood as meaning, for example, the natural cellulose fibre, such as cotton, linen and hemp, and also cellulose pulp and regenerated cellulose. The process of the invention is also suitable for treating hydroxyl-containing fibres present in blend fabrics, for example, blends of cotton with polyester fibres or polyamide fibres.

The fibre materials used have a density of between 30 and 200g/m², preferably between 100 and 150 g/m², the porosity of the material lying in the range of 0.1 to 3%, preferably 0.1 to 1.5%.

Preferably, the cellulosic fibre material used is cotton or a cotton blend.

The fibres mentioned may be present in various forms, for example, as staple or yarns or as wovens or knits.

A further aspect of the invention, as previously mentioned, is to provide excellent sun protection factors for cellulosic fibre materials by the combined use of a fluorescent whitening agents of formula (1) and a UV absorber. Usually little or no observable reduction of the degrees of whiteness of the so-treated materials results.

For this purpose, application of the UV absorber may be performed before, during or after treatment of the material with the FWA of formula (1).

Any UV absorber suitable for cellulosic fibre materials may be applied for this purpose. The UV absorber used may be, e.g., an o-hydroxybenzophenone, an o-hydroxy-phenylbenzotriazole, a 2-aryl-2H-benzotriazole, a salicylic acid ester, a substituted acrylonitrile, a substituted acrylaminoethylene, a nitrilohydrazone, o-hydroxyaryl-1,3,5-triazine, a sulphonated 1,3,5-triazine or preferably an oxalic anilide.

Preferably reactive UV absorbers are used and particularly preferred are the UV absorbers described in the U.S. Pat. No. 5,700,295, especially the oxalic anilides.

Especially preferred as UV absorber are the compounds of formula:

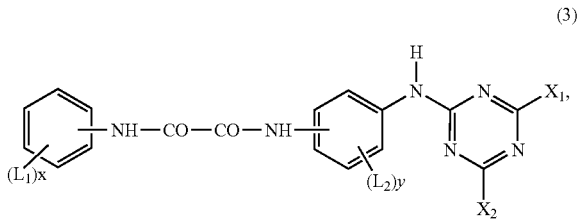

(3)

whereby $L_1$ and $L_2$ independently of each other are hydrogen, sulpho, hydroxy, $C_1$-$C_4$-alkyl or $C_1$-$C_{12}$-alkoxy, x and y independently of each other are 1, 2 or 3, $X_1$ chloro oder fluoro and $X_2$ a reactive radical of the formula

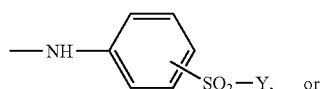

(4)

or

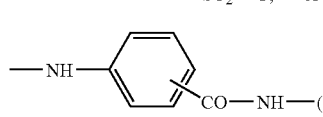

(5)

is, wherein Z is a fibre-reactive group and n is 2 or 3.

A fibre-reactive group is to be understood as meaning such a group which is capable of reacting with the hydroxyl groups of the cellulosic fibre or with the amino groups of polyamide fibre materials to form covalent chemical bonds. Many such reactive groups are known, in particular from the chemistry of the so-called "reactive dyes". However, within the scope of the present invention, preferred fibre-reactive groups Z are those in which Z is a radical of the formula:

—$SO_2$—Y'    (6),

—$SO_2NH$—Y'    (7),

—$NHCO(CH_2)_3SO_2$—Y'    (8),

—$CONH(CH_2)_2SO_2$—Y'    (9) or

—NHCO—Y'    (10),

Y' representing vinyl, β-sulphatoethyl, β-thiosulphatoethyl, β-phosphatoethyl, β-acyloxyethyl or β-haloethyl, especially those in which Z is a radical of formula (6) and Y represents —$CH_2CH_2OSO_3M$, M being as defined previously.

The application of the FWA's and also, when desired, the UV absorbers can take place by an exhaust or continuous process as well known from the literature for similar compounds.

In the exhaust process the liquor ratio can be chosen within a wide range, for example, from 3:1 to 200:1, preferably from 10:1 to 40:1. It is advantageous to operate at a temperature of 20 to 120° C., preferably 40 to 110° C.

The fibre-reactive UV absorbers are applied advantageously in the presence of acid-binding agents, for example, sodium hydroxide, sodium carbonate, sodium bicarbonate, sodium formate, potassium carbonate, sodium silicate, sodium trichloroacetate or sodium triphosphate, in the presence or absence of neutral salts, for example, sodium sulphate or sodium chloride.

The quantities of the UV absorbers to be applied to the cellulosic material according to the process of the invention may vary over a wide range. However, when used in amounts of between 0.005 and 1% by weight, based on the weight of the fibre material, useful effects may be obtained. Preferably, however, the amount of the compound of formula (1) used is from 0.01 to 0.5% by weight, based on the weight of the fibre material.

In the continuous process, the liquor add-on is advantageously 40-700, preferably 40-500, % by weight. The fibre material is then subjected to a heat treatment process to fix the applied FWA's and UV absorbers. This fixing can also be effected by the cold batching method.

The heat treatment preferably takes the form of a steaming process in a steamer with ordinary or superheated steam at a temperature of 98 to 105° C. for, for example, 1-7, preferably 1-5 minutes. The fixing of the UV absorber by the cold batching process can be effected by storing the impregnated and preferably rolled-up material at room temperature (15 to 30° C.) for 3 to 24 hours, for example, the cold batching time being known to depend on the UV absorber.

On completion of the application process and fixation, the treated materials are conventionally rinsed, soaped, for example, for 20 minutes at 90° C. with a solution containing 1 g/l. of calcined sodium carbonate, and dried.

The treatment bath may optionally contain other customary auxiliaries, for example, levelling, wetting deaerating and antifoaming agents, penetration accelerants or crease resisting agents.

The cellulose fibre materials treated by the process of the present invention possess high sun protection factors. The sun protection factor is defined as the ratio of the harmful dose of UV energy on protected skin to the harmful dose of UV energy on unprotected skin. Accordingly, a sun protection factor is also a measure of the transmissivity of fibre materials untreated and of those treated with FWA's and reactive UV absorbers described in this invention.

The sun protection factor can be determined, for example, by the method described by B. L. Diffey and J. Robson in J.Soc.Cosmet.Chem., 40, 127-133 (1989).

Some of the fluorescent whitening agents of formula (1) are known, the specific compounds of formula (11), however, are new and are a further subject of the present invention. The invention thus also provides compounds of formula

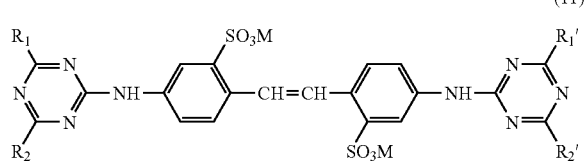

in which M is hydrogen, an alkali metal atom, ammonium or a cation formed from an amine;

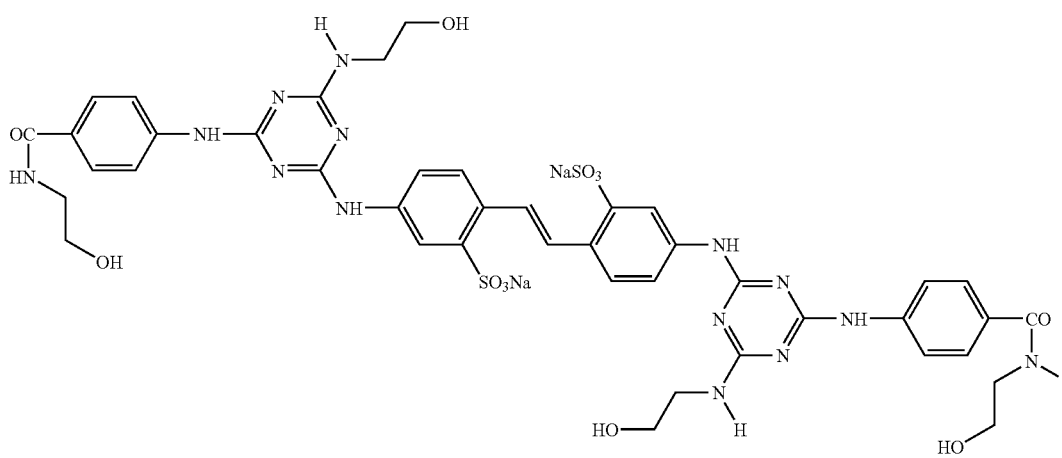

$R_1$ and $R_1'$ independently of each other are hydrogen, hydroxy, optionally substituted alkyl, 4-morpholinyl, —NH—$R_3$, —N($R_3$)$_2$ or —O—$R_3$, wherein $R_3$ is optionally substituted alkyl or optionally substituted aryl, $R_2$ is a group of formula

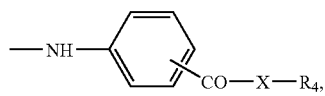

wherein X is —O— or —NH— and $R_4$ is $C_1$-$C_4$-alkyl which carries at least one hydrophilic substituent and $R_2'$ has the meaning of $R_1$ or $R_2$ with the proviso that the compound of formula (1), wherein $R_1$ and $R_1'$ are each hydroxyethylamino and $R_2$ and $R_2'$ are each phenylamino which is substituted in p-position with hydroxyethyl-aminocarbonyl is excluded.

The compounds of formula (1) can be prepared by known methods, e.g., by reacting, under known reaction conditions, cyanuric chloride, successively, in any desired sequence, with each of an aminostiibene-disulfonic acid and compounds capable of introducing the groups $R_1$, $R_1'$, $R_2$ and $R_2'$.

The compounds of formula (1) exhibit distinguished solubility In water combined with good affinity to cellulosic fibre material and aqueous formulations containing these compounds have excellent storage stability.

Especially if applied together with a UV absorber they confer to the cellulosic material excellent sun protection and a high degree of whiteness.

The UV absorbers of formula (3) are known or may be prepared by known methods.

The examples which follow illustrate the invention; parts and percentages are by weight unless otherwise stated.

EXAMPLE 1

Preparation of the Compound

1. Step 214 g water was added to a laboratory reaction flask, followed by 4 g sodium chloride. Contents of the reaction flask were chilled to 10° C. using an ice bath. To the reaction flask was added 15.6 g cyanuric chloride slowly in 10 minutes. After all of the cyanuric chloride was added, a white suspension was formed, pH of the flask contents was 3.10.

To the reaction flask, still at 10° C. was added 140 g of a 12% (wt./vol. 9 solution of 4,4'-diaminiostiblene-2,2'-disulfonic acid sodium salt (DAS) over a 1 hour period. After the addition was complete, the reaction mixture was held for another 50 minutes. The pH increased to 4.42. The pH was controlled between 3 and 4.5 during the reaction using 2.77 g 20% wt./vol. (17% wt./wt.) sodium carbonate. Contents of the flask were light orange in color with the suspension having good stirability. HPLC verified that the reaction was complete, 96-97% purity.

2. Step

In a laboratory flask was placed 60 g water and 4 g sodium chloride. Then 15.92 g 4-amino-N-(2-hydroxyethyl)-benzamide was added to form a suspension. The suspension was heated to 60° C. with stirring. After 15 minutes the suspension dissolved with the pH being 8.5. The aqueous suspension from the first reaction step, still at 16° C., was added to the aqueous solution of the benzamide over a 30 minute period. After the first 100 mL added, a bright yellow suspension was formed and the agitation was increased to compensate for the viscosity increase. The temperature of the reaction flask was maintained at 60° C. and pH was controlled between 6.5-7.0 using 1 M sodium carbonate. When the addition was complete, the reaction mixture was stirred for another 1 hour at 60° C. HPLC showed that the reaction was complete, 94-95% purity. Temperature of the reaction mixture was increased to 90° C. The viscosity of the reaction mixture increased and the pH dropped to 5.32. pH was adjusted with 1 M sodium carbonate to 6.0.

3. Step:

An aqueous solution was prepared by diluting 5.98 g ethanolamine with 15 g water. The aqueous ethanolamine solution was added to the second step reaction product, slowly over a 2 hour period at 90° C. pH was controlled between 7.5 and 8.0 by the addition of ethanolamine. During the addition, two phases were present. After the addition of ethanolamine, the reaction mixture was held at 90° C. with stirring. 25.2 g 32% wt./wt. sodium hydroxide was used to make sure that the pH of the reaction mixture was maintained above 7.0. After 6.5 hours, HPLC Indicated that the reaction was complete, 93% pure.

Still at 90° C., 8.4 g 37% wt./wt. HCl was added. The pH dropped from 7 to 4.5 and precipitate formed in 5 minutes. After the addition of HCl, the reaction mixture was stirred for 30 minutes. Then the reaction mixture was filtered hot through a warmed funnel. The filter cake was washed with water at 60° C., water at 40° C. and finally with water at room temperature. The filtrate was tested for the presence of chloride with sodium nitrate and then dried to constant weight. The product of formula (101) was obtained as a yellow in a yield of 95-98%:

EXAMPLES 2-6

Following the procedure of Example 1, the following compounds can be prepared:

| Example | $R_1$ and $R_1'$ | $R_2$ and $R_2'$ |
|---|---|---|
| 2 | —N(CH$_2$—CH(OH)—CH$_3$)$_2$ |  |
| 3 | —NH—CH$_3$ |  |
| 4 | —NH—CH$_3$ | 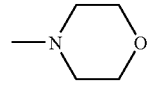 |
| 5 |  |  |
| 6 | —N(CH$_2$—CH$_2$—OH)$_2$ | 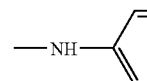 |

EXAMPLES 7 and 8

Following the procedure of Example 1, the following compounds can be prepared:

| Example | $R_1$ and $R_1'$ | $R_2$ | $R_2'$ |
|---|---|---|---|
| 7 | —NH—CH$_3$ | 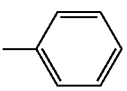 | |
| 8 | —NH—CH$_2$—CH$_2$—OH | 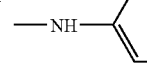 | |

EXAMPLE 9

Two samples each of 10 g. of a pre-washed cellulose fabric (cotton cretonne) are treated in an AHIBA® dyeing machine for 60 minutes at 95° C. at a liquor ratio of 1:20 in two different aqueous liquors.

A) 3.0 ml/l hydrogen peroxide 35%
2.0 ml/l sodium silicate 38° Bé
2.0 ml/l caustic soda 36° Bé
0.5 g/l ULTRAVON EL B) The same liquor as in A), but containing additionally 0.012% compound of formula (101) according to Example 1.

The results are given in the following table:

| Example | WG (Ganz)* | SPF value** |
|---|---|---|
| 9 A) | 83 | 3.3 |
| 9 B) | 222 | 23.7 |

*Whiteness degree: according to Ganz
**Sun Protection Factor (SPF): according to AS/NZS 4399:1996, Melbourne sunlight (average of 4 measurements)

The above results clearly demonstrate the substantial Improvement in sun protection factor attained by the use of compound (101).

EXAMPLE 10

If the procedure of Example 9 is repeated, but with samples of different cellulose fabric (cotton poplin) the results of the following table are obtained.

| Example | WG (Ganz)* | SPF value** |
|---|---|---|
| 10 A) | 82 | 3.5 |
| 10 B) | 220 | 46.7 |

*Whiteness degree: according to Ganz
**Sun Protection Factor (SPF): according to AS/NZS 4399:1996, Melbourne sunlight (average of 4 measurements)

The above results clearly demonstrate the substantial improvement in sun protection factor attained by the use of compound (101).

EXAMPLE 11

Two samples each of 10 g. of a pre-washed cellulose fabric (cotton cretonne or cotton poplin, respectively) are treated in an AHIBA® dyeing machine for 60 minutes at 95° C. at a liquor ratio of 1:20 in an aqueous liquor containing:

3.0 ml/l hydrogen peroxide 35%
2.0 ml/l sodium silicate 38 °Bé
2.0 ml/l caustic soda 36 °Bé
0.5 g/l ULTRAVON EL The samples are then treated for 10 minutes at 40° C. at a liquor ratio of 1:20 in a fresh bath containing 0.01% (relative to the weight of the fabric) of the compound of the formula

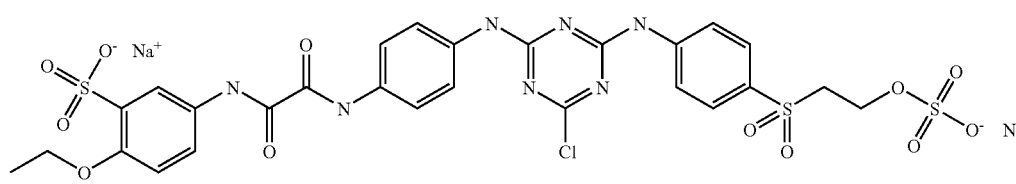

(102)

The temperature Is then raised to 95° C., g/l Glauber's salt (anhydr.) are added and the temperature is kept for 30 minutes. Then 10 g/l soda ash are added and after 20 minutes 0.2% (relative to the weight of the fabric) of the compound of the formula (101) according to example 1. After further 30 minutes at 95° C. the bath is cooled down, the fabric rinsed and dried. The results obtained are shown in the following table:of the following table are.

| Example | Fabric | WG (Ganz)* | SPF value** |
|---|---|---|---|
| 11 A) | Cotton-cretone | 204 | 32.7 |
| 11 B) | Cotton-Poplin | 205 | 71.2 |

*Whiteness degree: according to Ganz
**Sun Protection Factor (SPF): according to AS/NZS 4399:1996, Melbourne sunlight (average of 4 measurements)

The above results clearly demonstrate the additional improvement (compared to examples 9 and 10) in sun protection factor attained by the additional use of compound (102), whilst the degree of whiteness of the treated fabrics is not dramatically reduced.

The invention claimed is:

1. A process for improving the sun protection factor (SPF) of cellulosic fibre materials selected from cotton and cotton blends, which process comprises contacting said materials with at least one compound of the formula (1)

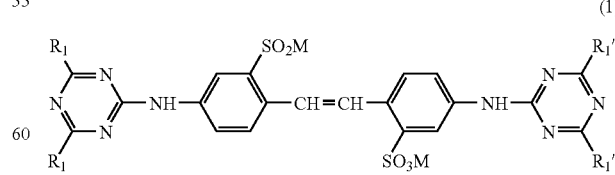

(1)

in which M is an alkali metal atom, ammonium or a cation formed from an amine;

$R_1$ and $R_1'$ independently of each other are hydrogen, hydroxy, optionally substituted alkyl, 4-morpholinyl, —NH—$R_3$, —N($R_3$)$_2$ or —O—$R_3$, wherein $R_3$ is optionally substituted alkyl or optionally substituted aryl, $R_2$ is a group of formula (2)

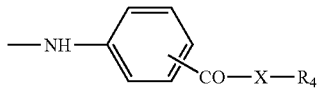

(2)

wherein X is —NH— and $R_4$ is $C_1$-$C_4$-alkyl which carries at least one hydrophilic substituent —OM and $R_2'$ has the meaning of $R_1$ or $R_2$, and further contacting said materials with at least one UV absorber of the formula (3)

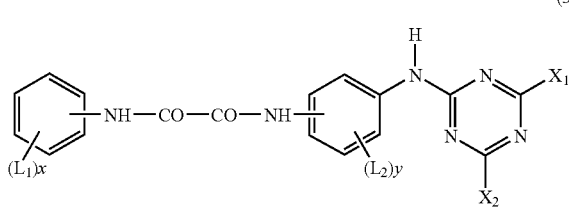

(3)

where
$L_1$ and $L_2$ independently of each other are hydrogen, sulpho, hydroxy, $C_1$-$C_4$-alkyl or $C_1$-$C_{12}$-alkoxy,
x and y independently of each other are 1, 2 or 3,
$X_1$ is chloro or fluoro and
$X_2$ is a reactive radical of the formula (4) or (5)

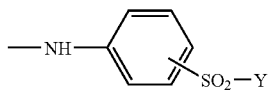

(4)

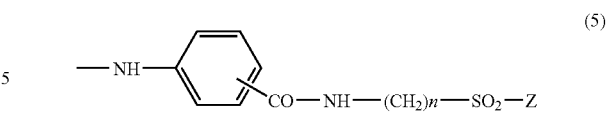

(5)

wherein Z is a fibre-reactive group and n is 2 or 3 and
Y is —$CH_2CH_2OSO_3M$.

2. A process according to claim 1 wherein, in the compound of formula (1), $R_1$ and $R_1'$ are identical.

3. A process according to claim 1, wherein, in the compound of formula (1), $R_1$ and $R_1'$ are hydrogen, hydroxy, optionally substituted alkyl, —NH—$R_3$, —N($R_3$)$_2$ or —O—$R_3$, wherein $R_3$ is optionally substituted alkyl or optionally substituted aryl.

4. A process according to claim 1, wherein, in the compound of formula (1), $R_1$ and $R_1'$ are hydrogen, hydroxy, unsubstituted $C_1$-$C_4$-alkyl or $C_1$-$C_4$-hydroxyalkyl, 4-morpholinyl, —NH—$R_3$, —N($R_3$)$_2$ or —O—$R_3$, wherein $R_3$ is unsubstituted $C_1$-$C_4$-alkyl or $C_1$-$C_4$-hydroxyalkyl or unsubstituted phenyl or phenyl substituted by sulfo.

5. A process according to claim 1, wherein the amount of the compound of formula (1) used is from 0.5 to 10% by weight, based on the weight of the fibre material.

6. A process according to claim 1, wherein the amount of the compound of formula (1) used is from 0.005 to 1% by weight, based on the weight of the fibre material.

7. A process according to claim 6, wherein the amount of the compound of formula (1) used is from 0.01 to 0.5% by weight, based on the weight of the fibre material.

8. A process according to claim 1, wherein the cellulosic fibre materials used have a density of between 30 and 200 g/m².

9. A process according to claim 1, wherein the cellulosic fibre materials used have a porosity of between 0.1 and 3%.

\* \* \* \* \*

UNITED STATES PATENT AND TRADEMARK OFFICE
CERTIFICATE OF CORRECTION

PATENT NO. : 7,425,222 B2
APPLICATION NO. : 10/504945
DATED : September 16, 2008
INVENTOR(S) : Georges Metzger et al.

It is certified that error appears in the above-identified patent and that said Letters Patent is hereby corrected as shown below:

Column 10
In claim 1, the structural formula (1) should read:

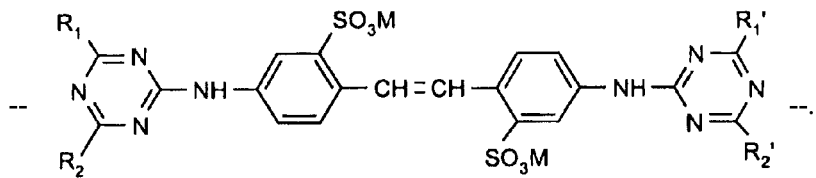

Signed and Sealed this

Ninth Day of December, 2008

JON W. DUDAS
*Director of the United States Patent and Trademark Office*